United States Patent
Caspary

(10) Patent No.: US 8,453,647 B2
(45) Date of Patent: Jun. 4, 2013

(54) DEVICE FOR PRESSURE EQUALIZATION ON A MEDICAL GAS DELIVERY MEANS

(75) Inventor: Renè-Christian Caspary, Lübeck (DE)

(73) Assignee: Dräger Medical GmbH, Lübeck (DE)

(*) Notice: Subject to any disclaimer, the term of this patent is extended or adjusted under 35 U.S.C. 154(b) by 370 days.

(21) Appl. No.: 12/958,483

(22) Filed: Dec. 2, 2010

(65) Prior Publication Data

US 2011/0168181 A1    Jul. 14, 2011

(30) Foreign Application Priority Data

Jan. 13, 2010    (DE) .................. 10 2010 004 424

(51) Int. Cl.
*A61M 16/00*    (2006.01)
*A61M 16/20*    (2006.01)

(52) U.S. Cl.
USPC ......... 128/205.24; 128/203.14; 128/204.18; 128/204.21; 137/87.03; 137/87.04; 137/102; 137/109

(58) Field of Classification Search
USPC ......... 128/203.14, 204.15, 204.18, 204.21, 128/204.26, 204.28, 205.24, 207.16; 137/87.03, 137/87.04, 102, 103, 109, 110, 111, 115.01, 137/115.05, 115.06, 115.13, 115.15, 115.16, 137/115.17, 115.18, 115.22, 462, 489.5, 137/493

See application file for complete search history.

(56) References Cited

U.S. PATENT DOCUMENTS

| | | | |
|---|---|---|---|
| 1,459,775 A | 6/1923 | Larner | |
| 4,823,828 A * | 4/1989 | McGinnis | 137/102 |
| 6,244,267 B1 * | 6/2001 | Eifrig | 128/202.22 |
| 6,338,339 B1 * | 1/2002 | Tsutsui et al. | 128/200.23 |
| RE37,989 E * | 2/2003 | Pedersen et al. | 137/471 |
| 6,877,511 B2 | 4/2005 | DeVries et al. | |
| 2002/0017301 A1 * | 2/2002 | Lundin | 128/205.24 |

FOREIGN PATENT DOCUMENTS

| | | |
|---|---|---|
| DE | 197 14 644 A1 | 10/1998 |
| DE | 10 2008 051 515 A1 | 4/2010 |
| GB | 2 324 122 A | 10/1998 |

* cited by examiner

*Primary Examiner* — Jackie Ho
*Assistant Examiner* — Gregory Winter
(74) *Attorney, Agent, or Firm* — McGlew and Tuttle, P.C.

(57) ABSTRACT

A device for passive pressure relief and for reducing the volume flow for an electromechanically driven medical gas delivery means (50) in a medical device for respirating a patient (60) with a pressure relief unit (1) with a first and second gas port (2, 3), with a relief valve (4), with a pressure relief outlet (8) with an equalization space (9) and with a nonreturn valve (11) and a valve disk (5), which is arranged in the relief valve (4) and is maintained in a position relative to a valve seat (7) via a bellows (60). The surfaces (51, 52) facing the first and second gas ports (2, 3) have different areas, so that the relief valve (4) opens as soon as an operating pressure (23) at the first gas port (2) exceeds a prevailing (stored) pressure level (24) in the equalization space (9).

20 Claims, 7 Drawing Sheets

DEVICE FOR PRESSURE EQUALIZATION ON A MEDICAL GAS DELIVERY MEANS

CROSS REFERENCE TO RELATED APPLICATIONS

This application claims the benefit of priority under 35 U.S.C. §119 of German Patent Application DE 10 2010 004 424.5 filed Jan. 13, 2010, the entire contents of which are incorporated herein by reference.

FIELD OF THE INVENTION

The present invention pertains to a device for pressure equalization and for the controlled reduction of a volume flow of an electromechanically driven medical gas delivery means to a medical device for respirating (also known as ventilating) a patient, especially a respirator or an anesthesia apparatus.

BACKGROUND OF THE INVENTION

Valves for pressure reduction are known as pressure reducers from the state of the art and are used for monitoring.

A respiration drive is designed in GB 2324122 B2 in the form of a radial flow compressor rotating at a high rpm. The respiration drive acts as a pressure source, which makes available a pressure rising with increasing rpm. Thus, the variation of the rpm is a manipulated variable for adapting the respiration pressure to the respiration situation, which means that the rpm must be cyclically increased and decreased again synchronously with the breathing cycle by varying the respiration pressure in such a way that the variation is resolved for individual breaths.

U.S. Pat. No. 6,877,511 BB describes a variation of the respiration pressure for the inspiration and expiration phases of a compressor, which variation is brought about by acceleration and deceleration of a rotary compressor.

In a medical gas delivery means driven electromechanically with variable air delivery capacity according to the state of the art, the particular pressure being currently delivered is brought about by varying the rpm as a function of an external actuating signal, for example, the signal of a respirator.

A medical gas delivery means driven electromechanically with variable air delivery capacity comprises in the sense of the present invention a gas delivery means, gas delivery device or gas delivery unit in an embodiment with an electromechanical blower drive, radial flow compressor, rotary compressor, or side channel compressor.

These variations of the rpm lead to accelerations and decelerations operations. The accelerations and decelerations of radial flow compressors and/or rotary compressors, which occur in a cumulative manner during the life of the product, impose very high requirements on temperature and media resistance, reliability and low wear for the components present in the device, such as shafts, bearings and seals, based on the intended use for supplying patients with clean breathing air. These requirements cannot be guaranteed in each application over the entire life of the product, so that some components must undergo maintenance or be replaced at certain time intervals.

If the electromechanically driven medical gas delivery means is not operated variably but without being affected by an external actuating signal, the electromechanically driven medical gas delivery means must be operated permanently at the maximum necessary pressure level, even in the case in which the medical device being supplied does not continuously call for this pressure level for respirating a patient or the outlet of the electromechanically driven medical gas delivery means is blocked from time to time by closed valves in the respirator.

Reliable self-cooling by the air stream being delivered is thus no longer available. The self-cooling by the air stream is essential especially if the radial flow compressor or rotary compressor is encapsulated in a housing part to achieve reduced noise generation. The temperature rise resulting herefrom leads to a thermal load for the components such as shafts, bearings and seals. Operation of the electromechanically driven medical gas delivery means without self-cooling is therefore disadvantageous with respect to the service life both for operation with and without variation of the rpm. An essential percentage of the wear is due to thermal load and to dynamic accelerations and deceleration operations brought about by the respiration control.

SUMMARY OF THE INVENTION

It is therefore advantageous to avoid dynamic accelerations and deceleration operations as much as possible. Increases in the respiration pressure to be applied can, of course, be brought about by increasing the rpm of a radial flow compressor, but the respiration pressure can also be reduced by pneumatically relieving the pressure into the environment. However, the pressure relief must not counteract an increase in the respiration pressure intended by the user and is imposed on the medical device for respirating a patient and should take place independently from an actuation by an external actuating signal and without actively actuated components as parts of the electromechanically driven medical gas delivery means.

The object of the present invention is to provide an overload protection for pressure equalization between an electromechanically driven medical gas delivery means and a medical device for respirating a patient.

According to the invention, a device is provided for pressure equalization for an electromechanically driven medical gas delivery means in a medical device for respirating a patient. The device has a pressure relief unit comprising a first gas port and a second gas port comprising a relief valve with a valve disk and a valve crater. The device has a pressure relief outlet, an equalization space and a nonreturn valve. The valve disk of the relief valve is in pneumatic connection with the electromechanically driven medical gas delivery means via a front-side area and via a rear-surface area. The front-side area is made larger than the rear-side area. A front-side force acts on the valve disk via the front-side area and a rear-side force acts via the rear-side area at an operating pressure and a pressure level in the equalization space. A distance between the valve disk and the valve crater is determined by the operating pressure and the pressure in the equalization space and by the ratio of the front-side surface having the area to the rear-side surface having the area and by the ratio of the front-side force to the rear-side force, so that a partial volume flow of a volume flow, which is adapted to the operating state of the medical device for respirating a patient and to the operating state of the electromechanically driven medical gas delivery means, flows off into the environment via a bypass stream branch, via the relief valve and the pressure relief outlet.

The device according to the present invention is arranged as a pressure relief unit in parallel arrangement in a bypass stream branch of a main stream branch carrying an air flow. The air flow is carried to a pressure sink through the main stream branch by an electromechanically driven medical gas delivery means, designed as a rotary compressor, side channel compressor or radial flow compressor. The pressure sink is a medical device for respirating a patient, especially a respirator or anesthesia apparatus. The medical device for respirating a patient takes a pressure from the electromechanically driven medical gas delivery means, which pressure varies cyclically with the respiration control, and this variation may also result in complete blockage of the main stream branch, besides in an unhindered, free flow from the medical device to the patient without an appreciable flow resistance or pressure drop up to the patient. The pressure relief unit comprises a relief valve, with a valve sealing element designed as a valve disk, with a flexible bellows and with a valve crater, a first gas port, a second gas port, a pressure relief outlet, an equalization space, as well as a nonreturn valve with a nonreturn valve sealing element and with a nonreturn valve crater (valve seat).

The valve disk is connected with the flexible bellows in such a way that the valve disk is arranged such that it is movable in the direction of the first gas port towards the valve seat. The compressed air pressure relief unit seals, with the relief valve, the amount of removed air into the bypass stream branch on the inlet side against the amount of air being delivered by the electromechanically driven medical gas delivery means in the main stream branch if the pressure sink calls for an amount of air from the electromechanically driven medical gas delivery means. The electromechanically driven medical gas delivery means, designed as a rotary compressor, side channel compressor or radial flow compressor, is cooled in this case by the flowing air stream, and the amount of heat generated in the interior of the housing of the gas delivery means is effectively removed by this self-cooling to the outside. The relief valve closes the pressure relief outlet in this case based on the prestress of the flexible bellows with the front side of the valve disk against the valve seat, so that no amount of air can escape into the environment via the pressure relief outlet. The front side of the valve disk seals off the amount of air in the first gas port via a front-side surface A1. The bellows arranged on the rear side of the valve disk is in pneumatic connection on the rear side with the amount of air in the second gas port of the pressure relief unit via a rear-side surface A2. The rear-side surface A2 opposing the amount of air present on the rear side is made smaller than the front-side surface A1 opposing the amount of air located on the front side.

The nonreturn valve with the nonreturn valve sealing element and with the nonreturn valve seat is arranged between the rear-side surface A2 of the valve disk with the bellows and the second gas port of the pressure relief unit. The nonreturn valve seat is arranged towards the second gas port of the pressure relief unit, so that the nonreturn valve element seals against this nonreturn valve seat in such a manner that no air flow is possible from the first gas port into the buffer volume in the direction of the second gas port of the pressure relief unit, but an amount of air and pressure levels corresponding to this amount of air can reach the buffer volume and hence the rear-side surface A2 of the valve disk from the second gas port.

If the pressure sink does not receive any volume flow from the electromechanically driven medical gas delivery means, i.e., the main stream branch is fully blocked on the outlet side, for example, by a closed dispensing valve in the medical device for respirating a patient, the relief valve is opened, so that air can reach the pressure relief outlet from the first gas port and can flow off into the environment. Without a gas flow through the pressure relief outlet, the amount of heat generated in the interior of the housing would not be able to be removed to the outside. Gas-delivering states are thus obtained for the electromechanically driven medical gas delivery means, in which the amount of air being delivered cools the electromechanically driven medical gas delivery means, both when the main stream branch is blocked by the dispensing valve of the medical device for respirating a patient via the pressure relief outlet and when the main stream branch is unblocked through the main stream branch itself.

The mode of operation of the pressure relief unit and of the individual components will be explained in more detail below based on this state as a first working point of an outlet-side blockage of the main stream branch with the main stream branch blocked and on a first operating pressure $p_{w,1}$ in the main stream branch.

A first front-side pressure $p_{F,1}$ corresponding to the first working operating pressure $p_{w,1}$ acts on the front-side surface A1 of the valve disk from the side of the first gas port.

A first rear-side pressure $p_{B,1}$ corresponding to the first operating pressure $p_{w,1}$ acts on the system comprising the valve disk and the bellows from the side of the second gas port on the rear-side surface A2.

A couple of forces acting in the opposite direction with $F_{F,1}$ on the front side of the valve disk and $F_{B,1}$ on the rear side of the valve disk is obtained via the surfaces A1 and A2 of the valve disk from the front-side pressure $p_{F,1}$ and the rear-side pressure $p_{B,1}$. Since the surface A1 of the valve disk acting on the front side is larger than surface A2 of the valve disk acting on the rear side, the valve disk is moved away from the sealing crater in the direction of the second gas port. The relief valve is thus open.

This means that when the main stream branch is closed, an amount of air corresponding to the amount of air being delivered from the pressurized gas source enters the environment via the pressure relief outlet through the bypass stream branch and the sealing crater (seat) from the electromechanically driven medical gas delivery means. The nonreturn valve is closed in this first working point, so that air can flow from the main stream branch via the second gas port into the buffer volume between the bellows and the valve disk and the nonreturn valve on the rear side of the valve disk, so that the first operating pressure $p_{w,1}$ is present in the buffer volume.

The conditions for triggering an opening operation of the relief valve can be summarily described in the general form as follows.

Starting from any desired operating pressure $p_{w,x}$, the amount of air removed by the pressure sink, i.e., a volume flow flowing through the main stream branch must drop to such an extent, or stop, that the operating pressure rises to a pressure $p_{w,y}$ in such a way that a force $F_{F,y}$, which is greater than the force $F_{B,x}$ acting on the rear side of the pressure disk and being due to a prevailing (stored) pressure value $p_{v,x}$ and the surface A2 acting on the rear side, is obtained via the surface A1 of the front side of the valve disk, which said surface acts on the front side, so that the relief valve partially or fully opens.

If an amount of air is taken from the medical device for respirating a patient, preferably a respirator or anesthesia apparatus, at a second working point, with the main stream branch not blocked, a second operating pressure $p_{w,2}$, which is a lower operating pressure than the first operating pressure $p_{w,1}$, becomes established in the main stream branch. A rear-side force $F_{F,2}$ acting on the valve disk of the relief valve results from the operating pressure $p_{w,2}$ and the surface A1 of the valve disk of the relief valve, which said surface acts on the front side. The pressure drop resulting in the main stream branch from the elimination of the blockage of the main stream branch causes a pressure difference at the nonreturn valve, so that the nonreturn valve sealing element of the nonreturn valve, which said element is preferably designed as a diaphragm, is pressed against the nonreturn valve seat and no pressure equalization to the main stream branch can take place via the second gas port of the pressure relief unit. The first operating pressure $p_{w,1}$ is thus maintained in the equalization space and it is stored in the equalization space as a pressure value $p_{V,1}$ almost without a time delay.

This stored (prevailing) pressure value $p_{V,1}$ continues to act unchanged on the rear side on the valve disk of the relief valve with the surface A2 of the relief valve such that there is a force $F_{B,1}$ on the valve disk acting on the rear side. The force ratios at the valve disk of the relief valve change due to the pressure change $p_{w,2}$.

The force $F_{B,1}$ acting on the rear side of the valve disk of the relief valve is now greater than the front-side force $F_{F,2}$, which results from the operating pressure $p_{w,2}$. This brings about closure of the relief valve.

After completion of the closing operation of the relief valve, the pressure $p_{V,1}$ in the equalization space is released by the relative motion of the bellows, which motion is coupled with the motion of the valve disk, to a pressure value $p_{v,1}$, which is slightly lower than the pressure level $p_{V,1}$ that was previously present.

The conditions for triggering a closing operation of the pressure relief valve can be summarily described in the general form as follows.

Starting from any desired operating pressure $p_{w,x}$, the amount of air removed by the pressure sink, i.e., a volume flow flowing through the main stream branch, must be so large that the operating pressure will drop to a pressure $p_{w,z}$, which results over the effective surface A1 of the front side of the valve disk in a force $F_{F,z}$ that is weaker than the force $F_{B,x}$ resulting from a prevailing (stored) pressure value $p_{v,x}$ and the surface A2 acting on the rear side on the rear side of the valve disk, so that the relief valve partly or completely closes.

The opening and closing characteristic of the relief valve is set by dimensioning surface A1 of the valve disk, which surface acts on the front side and surface A2 of the valve disk, which latter surface acts on the rear side and by the area ratio QA=A1/A2 resulting therefrom. Ratio QA is preferably selected in a range of 1.1 to 2.0 and especially preferably in a range of about 1.5 to 1.6. The front-side surface A1 preferably has a front-side surface A1 with an effective surface area of 60 mm² to 80 mm², and the front-side surface A1 is especially preferably designed with an effective surface area of 70 mm². The rear-side surface A2 preferably has an effective surface area of 35 mm² to 55 mm², and the rear-side surface A2 is especially preferably designed with an effective surface area of 45 mm². The opening and closing characteristic is adapted to the working pressure ratios arising from the combination of an electromechanically driven medical gas delivery means preferably designed as a radial flow compressor or rotary compressor and a pressure sink preferably designed as a medical device for respirating a patient and especially preferably as a respirator or anesthesia apparatus. A typical operating pressure for an electromechanically driven medical gas delivery means designed as a radial flow compressor for operating a respirator is in a range of 30 mbar to 60 mbar. A typical value at which the relief valve releases the pressure relief outlet and air streams from the main stream branch via the bypass stream branch into the environment is in the range of 70 mbar to 100 mbar.

The advantage of the relief valve according to the present invention over a solution with a pressure relief valve in which the pressure relief valve is opened beginning from a defined pressure (pressure limit) is the variability of the operating pressure. The relief valve functions at any desired working point of the electromechanically driven medical gas delivery means as long as the difference between the pressure levels $p_{w,1}$ and $p_{w,2}$ is great enough.

In a special embodiment, a dispensing element is present in the equalization space. This dispensing element guarantees that during changes in the operating pressure $p_{w,1}$, the corresponding prevailing (stored) pressure value $p_{V,1}$ in the equalization space can adapt itself to these changes. The adaptation takes place due to a pressure equalization towards the environment. The nonreturn valve would remain closed without a dispensing element in case of a decreasing operating pressure at a prevailing (stored) pressure value $p_{V,1}$ in the equalization space, which pressure value is higher than the operating pressure $p_{w,1}$. The force $F_{B,1}$ acting on the rear side of the valve disk of the relief valve would now be lastingly stronger than the front-side force $F_{F,2}$ that results from the operating pressure $p_{w,2}$, so that the relief valve would no longer open.

A dispensing element is necessary especially if the electromechanically driven medical gas delivery means shall not be operated statically at a working point with an operating pressure but at different working points with an operating pressure set continuously or in a stepwise variable manner.

The dispensing element is designed such that the pressure equalization time via the dispensing element is in the range of about 5 minutes in the case of the application in which the pressure sink is a medical device for respirating a patient, preferably a respirator, especially an intensive respirator. The dispensing element represents a pneumatic resistance R (resistance).

The following possibilities of technical solutions, for example, a dispensing diaphragm, an air-permeable membrane filter, a sintered filter or even combinations of sintered elements, membranes and diaphragm elements, may be considered for a practice-oriented implementation of the dispensing element. These possible solutions make it possible to generate a pneumatic resistance. A dispensing diaphragm is preferably used, and a dispensing diaphragm with round dispensing opening is especially preferred. The dispensing opening may be preferably prepared by machining by milling or by means of laser machining. Holes with a diameter in the range of a few μm can thus be prepared in a reproducible manner.

The duration is set by selecting a predetermined width of opening of the dispensing element combined with the volume contained in the equalization space.

The volume or its special pneumatic property, the compliance C, cooperates with the pneumatic resistance R as a pneumatic time constant τ.

$$\tau = R \cdot C$$

The compliance is determined here both by the volume contained in a space element or container and by the properties of the outer wall of a dispensing element predetermined in the space element or container. The compliance values needed for the application can be embodied by correspondingly selecting the material, for example, by using either an essentially flexible elastic material or a predominantly solid nonelastic material for the outer wall of the container in conjunction with the material thickness of the outer wall of the container. For the application of the pressure relief unit in a medical device for respirating a patient, the equalization process over time between the equalization space and the environment via the dispensing element shall have concluded completely with a duration of about 3 minutes to 5 minutes. Under the physically generally valid precondition that an equalization process is concluded at a rate of 95% with five times the duration of a time constant τ, a value of one minute is obtained for τ from an equalization time of 5 minutes.

With a pneumatic compliance C of $$C = 0.22 \frac{mL}{mbar}$$

which is predetermined by the dimensions and the material selected for the equalization space, a necessary pneumatic resistance R is obtained as $$R = 4545 \frac{mbar \cdot min}{L}$$

as the basis for dimensioning the dispensing element.

For an embodiment with a dispensing diaphragm, the width of opening of the opening in the dispensing diaphragm is preferably selected in the range of 0.002 μm² to 0.008 μm² for an equalization space of 0.2 L to 0.3 L resulting from the compliance indicated, which corresponds to a diameter of about 50 μm to 100 μm and results in a duration of about 5 minutes in case of a round dispensing opening.

In another embodiment, the dispensing element is not connected pneumatically with the environment, but the dispensing element is in connection via an equalization line with an air stream branch guiding the air flow from the gas delivery means to the medical device for respirating a patient. In an arrangement of the pressure relief unit in the bypass stream branch, the dispensing element is preferably in connection with the main stream branch or with the bypass stream branch via an equalization line. It is also preferable to connect the equalization line from the dispensing element pneumatically with the bypass stream branch in the direction of the medical device for respirating a patient, and it is also preferable to connect it with the second gas port of the pressure relief unit. Due to the pressure in the main stream branch and in the bypass stream branch being increased by approximately 30 mbar to 60 mbar relative to the environment and to a pressure level in a range of 70 mbar to 100 mbar being present in the equalization space before opening the relief valve and discharge via the pressure relief outlet, the pressure gradient between the equalization space and the pressure in the main stream branch or bypass stream branch is made lower by about 40% to 70% than the pressure difference between the pressure level in the equalization space and the environment. The consequence of this lower pressure gradient is that the equalization process takes place substantially more slowly in the main stream branch or bypass stream branch than a pressure equalization against the environment with equal dimensioning of the equalization space and dispensing element. In an inversion of the argument, the volume of the equalization space can thus be reduced at equal predetermined duration of the equalization process equaling 3 minutes to 6 minutes. The volume of the equalization space can thus be selected in a range below 0.1 L when dimensioning the time constant τ.

In another embodiment, the elastic bellows is designed such that it is free from prestress. Thus, the bellows does not act complement or counteract the forces $F_F$, $F_B$ acting on the front side and on the rear side, which forces result from the pressure values $p_{w,1}$, $p_{w,2}$ and the area ratio QA.

In a special embodiment, the elastic bellows is provided with a prestress. Thus, the bellows acts with or against the forces $F_F$, $F_B$ acting on the front side and on the rear side, which forces result from the pressure values $p_{w,1}$, $p_{w,2}$ and the area ratio QA. It is possible as a result to adapt the areas A1, A2 to the design needs; in particular, it is thus possible to reduce the rear-side area A2, because a part of the force $F_B$ acting on the rear side is applied by a prestress of the bellows, which is designed, for example, as a spring.

However, the prestress can also be set in a preferred embodiment by selecting the elasticity of the material and/or the thickness of the material of the bellows. In another preferred embodiment, it is possible to apply a nonlinear force component to the valve disk by means of the prestress of the bellows, besides the area ratio QA, which linearly applies a continuous force to the valve disk independently from the path of the bellows and the state, the force applied to the valve disk increasing with increasing path of the bellows, i.e., being designed as a force acting progressively.

The present invention will be explained in more detail with reference to the drawings attached, where identical reference numbers designate identical features. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
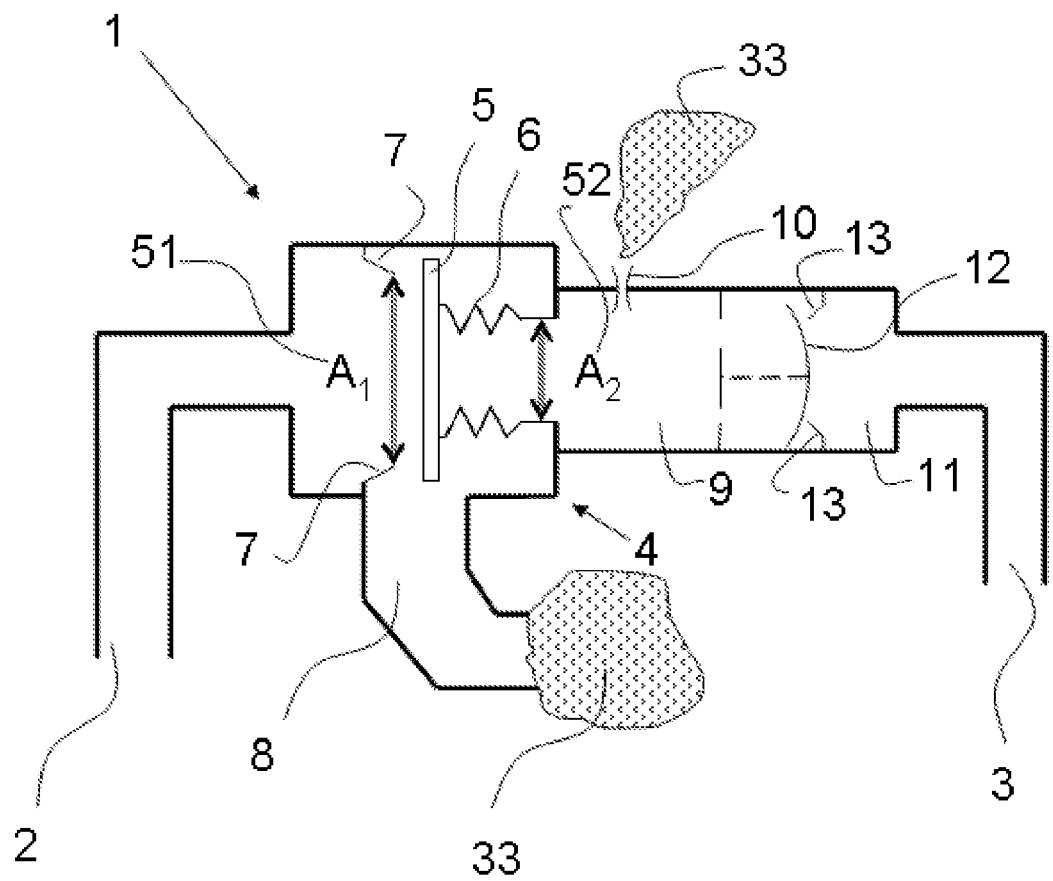
FIG. 1 is a schematic view showing the basic structure of a pressure relief unit according to the invention.

Referring to the drawings in particular, FIG. 1 shows a pressure relief unit 1 according to the present invention with a first gas port 2, with a second gas port 3, with a relief valve 4, comprising a valve disk 5, a flexible bellows 6 and a valve seat 7, with a pressure relief outlet 8 to an environment 33, with an equalization space 9, with a dispensing element 10, with a nonreturn valve 11, comprising a nonreturn valve sealing element 12 and a nonreturn valve seat 13. The pressure relief unit 1 is designed as follows.

Valve disk 5 is connected with the flexible bellows 6 in such a way that the valve disk 5 is arranged movably and is prestressed preferably in the direction of the valve seat 7, so that the valve disk 5 lies or almost lies on the valve seat 7 in a pressureless and flow-free state and the pressure relief outlet 8 is largely closed in the direction of the environment 33 in the pressureless and flow-free state. Valve disk 5 is in connection with the front-side surface 51 of valve disk 5, which said surface 51 has an area A1, via the first gas port 2. Valve disk 5 is in connection with the internal diameter of bellows 6 via the equalization space 9 and the nonreturn valve 11 is in connection with the rear-surface surface 52 of valve disk 5, which said surface 52 has an area A2. Pressure equalization continuously takes place between the equalization space 9 and the environment 33 via the dispensing element 10. The ratio of the front-side area A1 51 of valve disk 5 to the rear-side area A2 52 of the valve disk 5 is designed for a value in the range of 1.1 to 2.0. The front-side surface 51 with the area A1 of the valve disk 5 preferably has an effective surface of 60 mm² to 80 mm², and the rear-side surface 52 with the area A2 of the valve disk 5 preferably has an effective surface of 35 mm² to 55 mm².

Figure 2A:
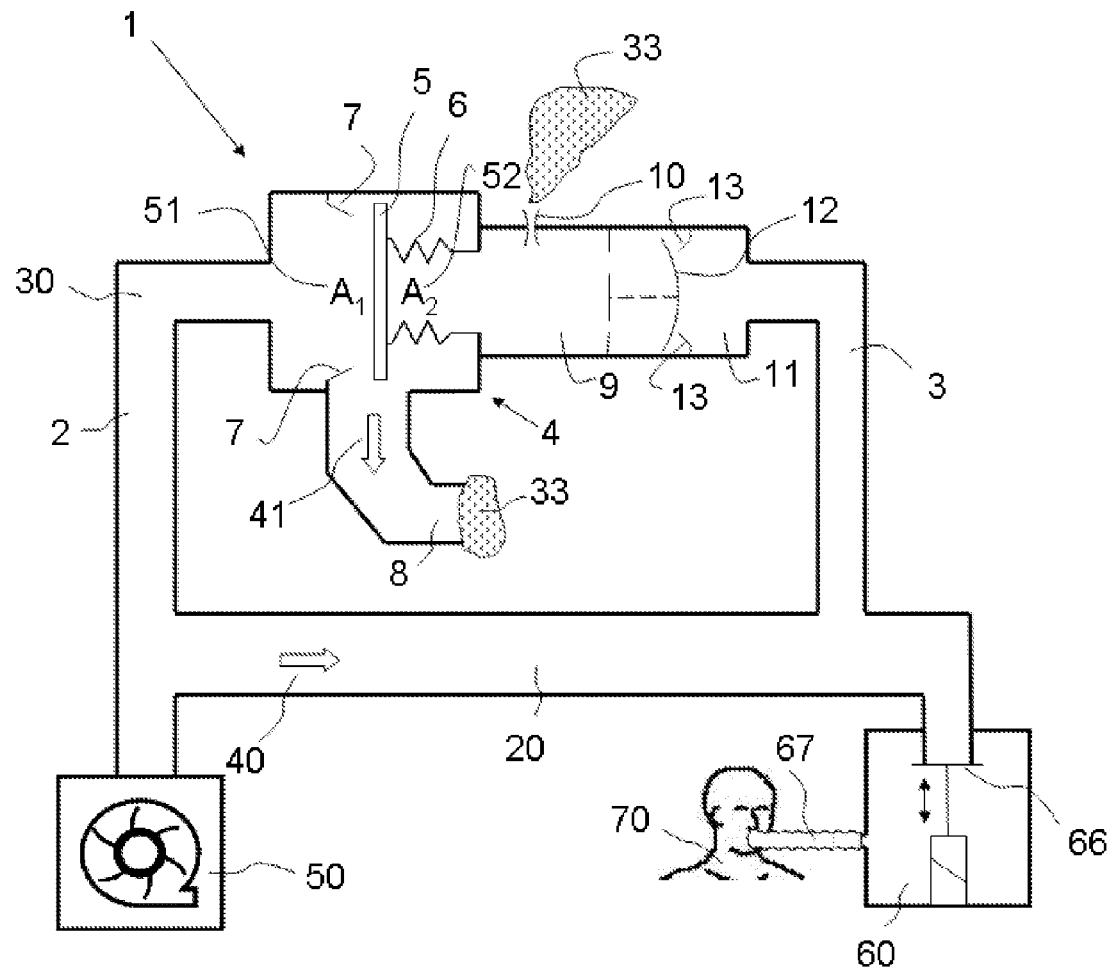
FIG. 2a is a schematic view showing the pressure relief unit according to FIG. 1 in a first view with an electromechanically driven medical gas delivery means with a respirator.
Figure 2B:
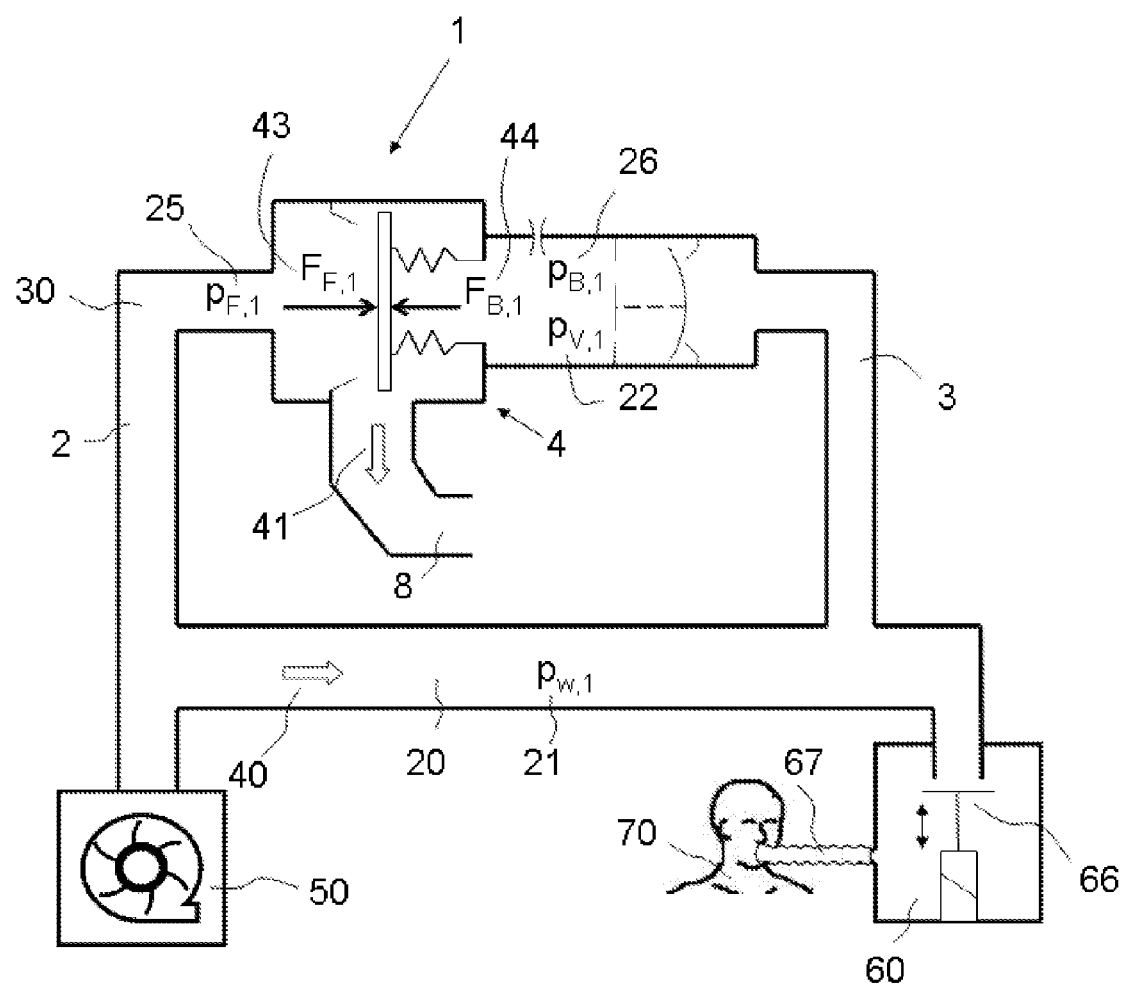
FIG. 2b is a schematic view showing the pressure relief unit according to FIG. 1 in the first view with the electromechanically driven medical gas delivery means with the respirator.

In FIGS. 2a and 2b, the pressure relief unit 1 according to FIG. 1 is arranged in parallel in a bypass stream branch 30 of a main stream branch 20 carrying an air flow 40 in a combination with a medical device for respirating a patient with pneumatic connection with a patient. The medical device for respirating a patient is shown in these FIGS. 2a and 2b in a schematic view as an example as a respirator 60. FIG. 2a shows the design features in a schematic view and shows the pressure relief unit 1 according to FIG. 1 in a first operating state. FIG. 2b additionally shows pressure ratios and force ratios, wherein the design features are identical to the features shown in FIG. 2a. Not all the design features shown in FIG. 2b are provided with reference numbers. The air flow 40 enters the pressure relief unit 1 to the relief valve 4 via the first gas port 2. Equalization space 9 is connected with the main stream branch 20 via the second gas port 3 and the nonreturn valve 11. A pressure equalization continuously takes place via the dispensing valve 10 between the equalization space 9 and the environment 33 (FIG. 1).

Identical elements in FIGS. 2a and 2b are designated by the same reference numbers as in FIG. 1.

A volume flow 40 is carried by the main stream branch 20 from an electromechanically driven medical gas delivery means 50 to a respirator 60. The respirator 60 removes a volume flow 40 from the electromechanically driven medical gas delivery means 50 and represents a pressure sink. Respirator 60 removes a volume flow 40 varying cyclically with the respiration of a patient 70 and/or the control of the respirator 60 from the electromechanically driven medical gas delivery means 50. The air is carried from the respirator to the patient 70 via feed lines 67. As a result, the pressure level $p_w$ in the main stream branch 20 and the bypass stream branch 30 varies cyclically with the respiration of the patient 70 and/or the control of the respirator 60. A typical operating pressure in the main stream branch 20 is in the range of 50 mbar to 80 mbar.

In this arrangement according to FIGS. 2a and 2b, the respirator 60 is in the first operating state, in which the respirator 60 does not take over any volume flow 40 from the electromechanically driven medical gas delivery means 50, during one time interval of the respiration cycle. The respirator 60 blocks the main stream branch 20 by closing means 66 present in the respirator 60. The operating pressure in the main stream branch 20 then rises to a value $p_{w,1}$ 21 of 70 mbar to 100 mbar.

Nonreturn valve 11 is open towards the second gas port 3 during this time interval of the respiration cycle, and a pressure equilibrium is obtained in this first operating state on the front side and the rear side of the valve disk 5. The current operating pressure $p_{w,1}$ 21 is present on the front side as a front-side pressure $p_{F,1}$ 25, and the current operating pressure $p_{w,1}$ 21 is present on the rear side of the valve disk 5 as a rear-side pressure $p_{B,1}$ 26, so that the pressure ratios in the relief valve 4 are equalized and the current operating pressure $p_{w,1}$ is also present as an identical pressure level $p_{V,1}$ 22 in the equalization space 9. The pressure level in the equalization space 9 becomes equalized with the pressure in the environment 33 with a time delay over several respiration cycles via the dispensing element 10 (FIG. 1).

The duration of this equalization process is selected in a range of about five minutes in an intensive respirator. This duration is set as a time constant τ via a predetermined pneumatic resistance R, for example, by a predetermined width of opening of dispensing element 10 and by the pneumatic compliance C of equalization space 9.

The pressure level $p_{V,1}$ in the equalization space 9, identical to the current operating pressure $p_{w,1}$ 21, is present as a rear-side pressure $p_{B,1}$ on the rear side at the valve disk 5.

A force $F_{F,1}$ 43 is obtained at the relief valve 4 via the surfaces 51, 52 of valve disk 5 with the areas A1, A2 and via the front-side pressure $p_{F,1}$ at the valve disk 5 on the front side of the valve disk 5, and a force $F_{B,1}$ 44 is obtained on the rear side of the valve disk with the rear-side pressure $p_{B,1}$. The front-side force $F_{F,1}$ 43 is greater than the rear-side force $F_{B,1}$ 44 at the pressure equilibrium existing in the first operating state between the front-side and rear-side pressures $p_{w,1}$ 21, $p_{B,1}$ 26 due to the fact that the front-side surface 51 of the valve disk 5, which said surface has the area A1, is larger than the rear-side surface 52 of valve disk 5, which said surface 52 has the area A2. When adding the forces $F_{F,1}$ 43 and $F_{B,1}$ 44 acting in opposite directions, a front-side force acting on the valve disk 5 is obtained in this constellation of forces as a resulting force, so that the valve disk 5 is moved away from the valve seat 7 and the pressure relief outlet 8 is released. A volume flow component 41 of the volume flow 40 thus flows via the opened relief valve 4 from the main stream branch 20 into the environment 33 via the bypass stream branch 30 through the pressure relief outlet 8.

Figure 3A:
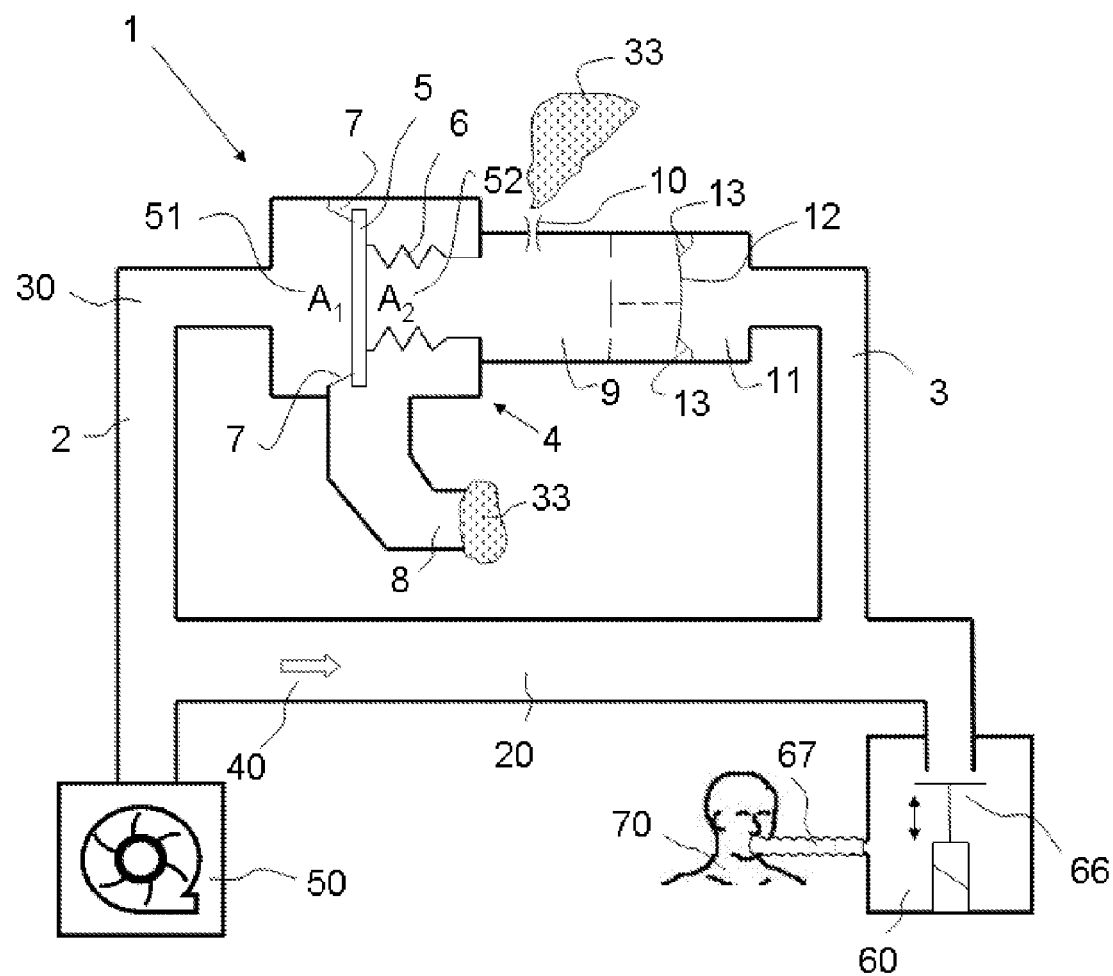
FIG. 3a is a schematic view showing the pressure relief unit according to FIG. 1 in a second view of the electromechanically driven medical gas delivery means and with the respirator.
Figure 3B:
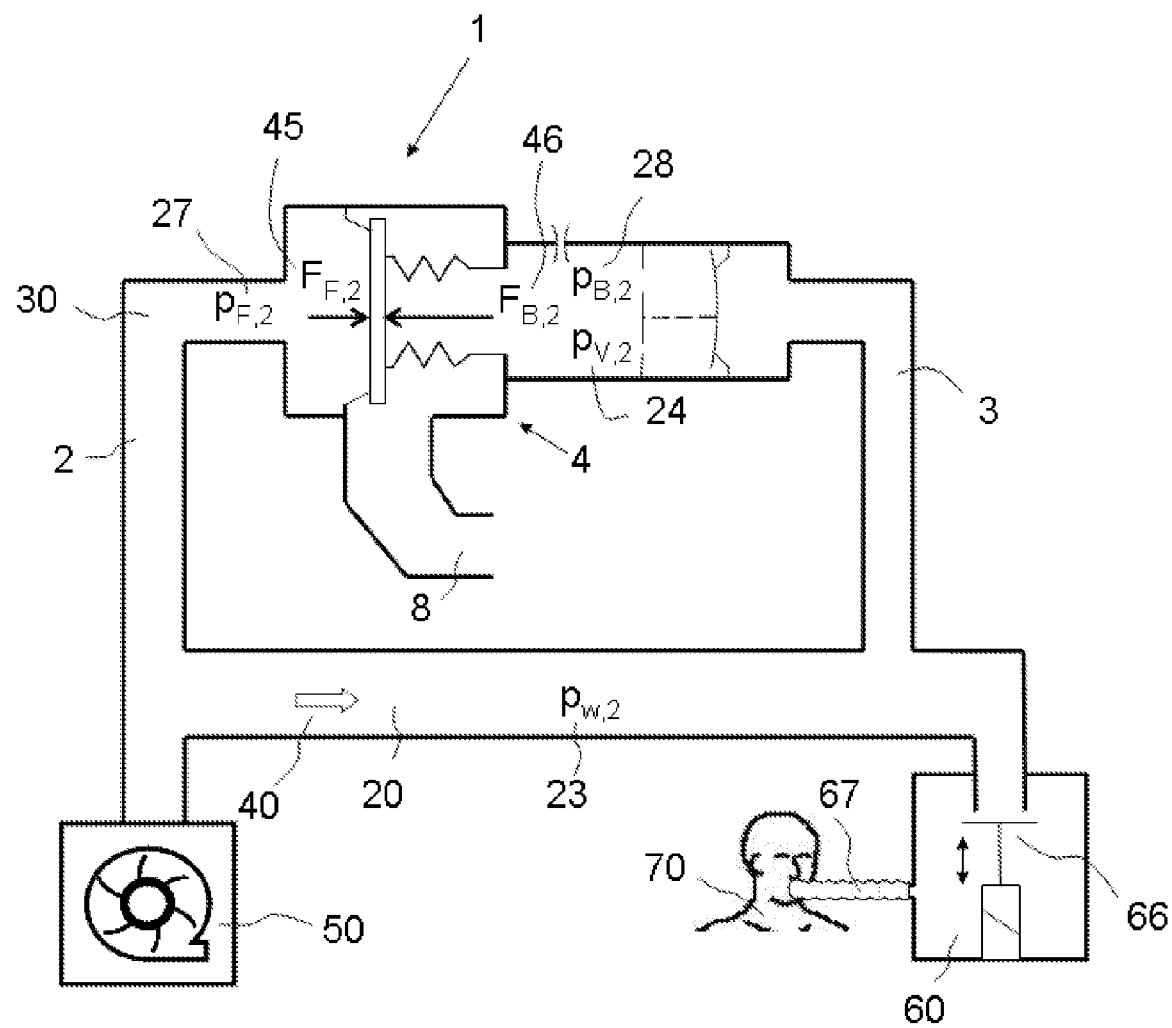
FIG. 3b is a schematic view showing the pressure relief unit according to FIG. 1 in the second view of the electromechanically driven medical gas delivery means and with the respirator.

In FIGS. 3a and 3b, the pressure relief unit 1 according to FIG. 1 is arranged in parallel in a bypass stream branch 30 of a main stream branch 20 carrying an air flow 40 in a combination with a medical device for respirating a patient with pneumatic connection with a patient. The medical device for respirating a patient is shown in these FIGS. 3a and 3b as an example as a respirator 60 in a schematic view. FIG. 3a shows in a schematic view the design features and shows the pressure relief unit 1 according to FIG. 1 in a second operating state. FIG. 3b additionally shows pressure ratios and force ratios, wherein the design features are identical to the features shown in FIG. 3a. Not all the design features shown in FIG. 3b are provided with reference numbers. The air flow 40 enters via the first gas port 2 and the pressure relief unit 1 to the relief valve 5. The equalization space 9 is connected with the main stream branch 20 via the second gas port 3 and the nonreturn valve 11. Pressure equalization continuously takes place between equalization space 9 and the environment 33 via the dispensing element 10.

Identical elements in FIGS. 3a and 3b are provided with the same reference numbers as in FIG. 1.

A volume flow 40 is sent through the main stream branch 20 from an electromechanically driven medical gas delivery means 50 to a respirator 60. The respirator 60 removes a volume flow 40 from the electromechanically driven medical gas delivery means 50 and represents a pressure sink. The respirator 60 removes a volume flow 40 varying cyclically with the respiration of a patient 70 and/or the control of the respirator 60 from the electromechanically driven medical gas delivery means 50. The air is sent from the respirator to the patient 70 via feed lines 67. As a result, the pressure level $p_w$ in the main stream branch 20 and the bypass stream branch 30 varies cyclically with the respiration of the patient 70 and/or the control of the respirator 60.

In this arrangement according to FIGS. 3a and 3b, the respirator 60 is in the second operating state during a time interval of the respiration cycle, in which operating state the respirator 60 removes a volume flow 40 from the electromechanically driven medical gas delivery means 50.

Respirator 60 sends the volume flow 40 from the main stream branch 20 via feed lines 67 to the patient 70. Closing means 66 present in the respirator 60 does not bring about any blockages of the main stream branch 20 during the current time interval of the respiration cycle. A typical operating pressure $p_w$ in the main stream branch 20 is in the range of 50 mbar to 80 mbar.

Due to the fact that the equalization space 9 has been placed under the pressure level $p_{V,1}$ via the second gas port 3 in a state such as the state described in connection with FIGS. 2a and 2b, due to the respiration cycle, recurring in time immediately before this current time interval, the pressure level $p_{V,1}$ 22 still continues to be present in the equalization space 9 even during this current time interval of the respiration cycle and acts as a rear-side pressure $p_{B,2}$ 28. This pressure level $p_{V,1}$ 22 or the rear-side pressure $p_{B,2}$ 28 is higher than the current operating pressure $p_{w,2}$ 23 currently present now in the main stream branch 20 and the bypass stream branch 30. The nonreturn valve 11 thus closes with the nonreturn valve sealing element 12 against the nonreturn valve seat 13 and the connection between the equalization space 9 and the second gas port 3 is interrupted and the pressure level $p_{V,1}$, continues to prevail (be stored) in the equalization space 9.

The pressure level $p_{V,1}$ that has hitherto been present in the equalization space 9 becomes equalized with the pressure in the environment 33 (FIG. 1) with a time delay over several breathing cycles via the dispensing element 10 until a pressure level $p_{V,2}$ 24 is reached in the equalization space 9.

The duration of this equalization process is selected in a range of about 5 minutes in an intensive respirator. This duration is set via a predetermined resistance R, for example, by a predetermined width of opening of the dispensing valve 10 and by the pneumatic compliance C of the equalization space 9.

The operating pressure $p_{w,2}$ 23 currently present now acts as a front-side pressure $p_{F,2}$ 27 on the front side on the valve disk 5. Due to the fact that the pressure level $p_{V,1}$ 22 prevailing (being stored) as a rear-side pressure $p_{B,2}$ 28 is higher than the current operating pressure $p_{w,2}$ 23 currently present in the main stream branch 20 and the bypass stream branch 30, different force ratios are obtained at the relief valve 4. A force $F_{F,2}$ 45 acts on the front side of the valve disk 5 and the rear-side force $F_{B,2}$ 46 acts on the rear side of the valve disk via the surfaces 51, 52 with the areas A1, A2 and the pressure ratio from the pressure level $p_{V,1}$ 22 in the equalization space 9 as the rear-side pressure $p_{B,2}$ 28 and the current operating pressure $p_{w,2}$ 23. The rear-side force $F_{B,2}$ acting now is unchanged in this second operating state compared to the rear-side force $F_{B,1}$ 44 acting in the first operating state, because the pressure level $p_{V,1}$ 22 has been stored due to the closing of the nonreturn valve 11 in the equalization space 9 and continues to be present as a rear-side pressure $p_{B,2}$ 28 on the rear side of the valve disk 5. The front-side force $F_{F,2}$ 45 is lower in this second operating state than the rear-side force $F_{B,2}$ 46 acting in the first operating state due to the reduction of the operating pressure from $p_{w,1}$ 21 to a pressure level $p_{w,2}$ 23 with the front-side pressure $p_{F,2}$ 27 resulting therefrom. When adding the opposite forces $F_{F,2}$ 45 and $F_{B,2}$ 46, a front-side force acting on the valve disk 5 is obtained in the constellation of forces as a resulting force, so that the valve disk 5 is moved with the elastic bellows 6 in the direction of the valve seat 7.

This results in closing of the relief valve 4, and the pressure relief outlet 8 is largely closed against the environment 33, so that the volume flow 40 flows nearly completely from the electromechanically driven medical gas delivery means 50 through the main stream branch 20 to the respirator 60 and no volume flow component 41 (FIGS. 2a and 2b) of the volume flow 40 is sent into the environment 33.

Figure 4:
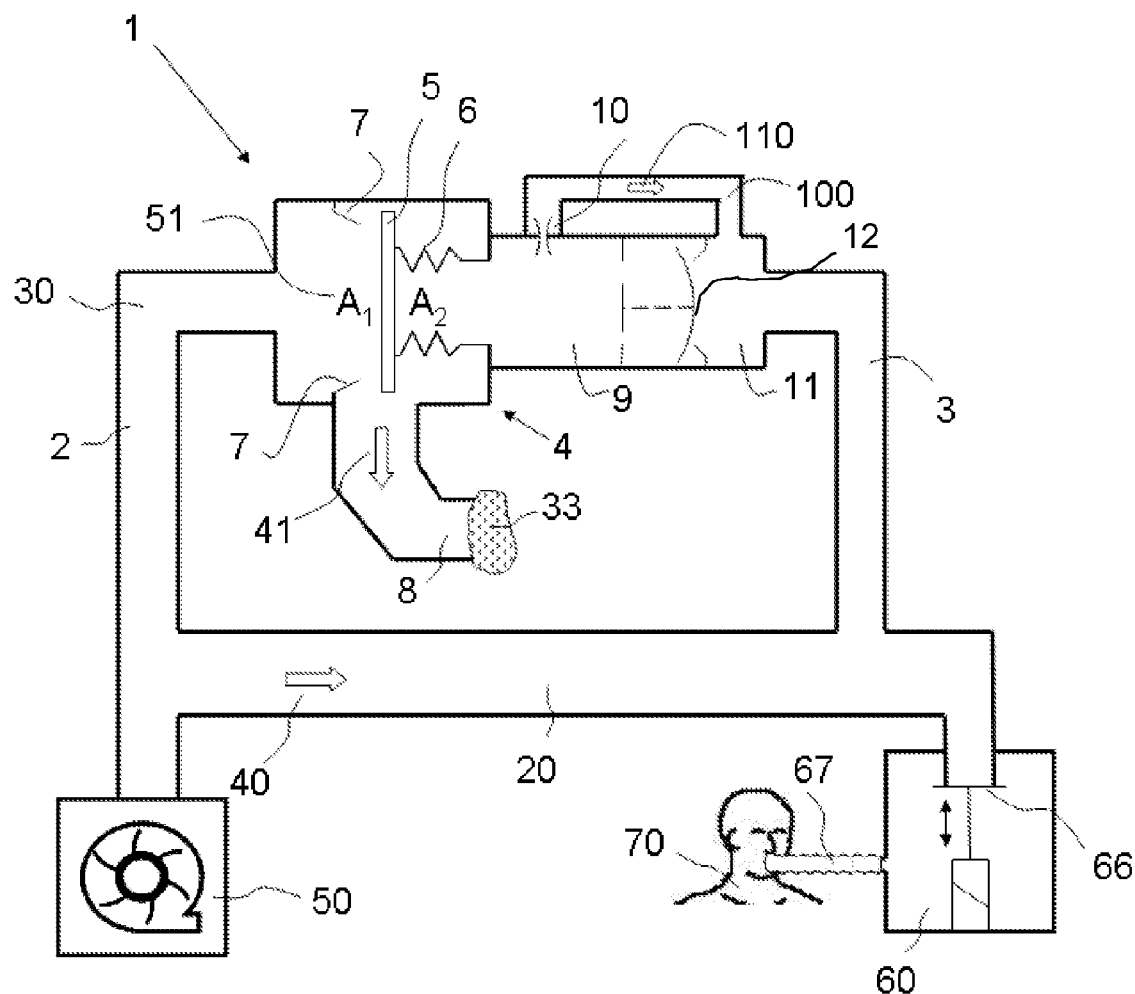
FIG. 4 is a schematic view showing a variant of the pressure relief unit according to FIG. 1 with an electromechanically driven medical gas delivery means and with a respirator.

A special variant of the pressure relief unit 1 according to FIG. 1 is shown in FIG. 4 arranged in parallel in a bypass stream branch 30 of a main stream branch 20 carrying an air flow 40 in a combination with a medical device for respirating a patient with pneumatic connection with a patient.

In a schematic view, FIG. 4 shows the design features and the designation of the pressure relief unit 1 according to FIG. 1 in the first operating state, wherein the medical device for respirating a patient is shown in a schematic view as an example as a respirator 60.

Identical elements in FIG. 4 are designated by the same reference numbers as in FIG. 1.

The air flow 40 enters the pressure relief unit 1 and reaches the relief valve 4 via the first gas port 2. The equalization space 9 is connected with the main stream branch 20 via the second gas port 3 and the nonreturn valve 11.

A volume flow 40 is sent through the main stream branch 20 from an electromechanically driven medical gas delivery means 50 to a respirator 60. The respirator 60 removes a volume flow 40 from the electromechanically driven medical gas delivery means 50 and represents a pressure sink. The respirator 60 removes a volume flow 40 varying cyclically with the respiration of a patient 70 and/or the control of the respirator 60 from the electromechanically driven medical gas delivery means 50. The air is sent via feed lines 67 to the patient 70 from the respirator.

Pressure equalization continuously takes place between the equalization space 9 and the second gas port 3 via the dispensing element 10 by means of an equalization line 100.

In this arrangement according to FIG. 4, the respirator 60 is in an identical operating state as in the arrangement according to FIGS. 2a and 2b. The pressure relief unit 1 is shown in a first operating state in a time interval of the respiration cycle, in which the respirator 60 does not take over any volume flow 40 from the electromechanically driven medical gas delivery means 40. The respirator 60 blocks the main stream branch 20 by closing means 66 located in the respirator 60.

The nonreturn valve 11 is opened towards the second gas port 3 during this time interval of the respiration cycle, and a pressure equilibrium is obtained in this first operating state on the front side and the rear side of the valve disk 5, so that the pressure ratios are equalized in this relief valve 4 and the current operating pressure is also present as an identical pressure level in the equalization space 9. The equalization space 9 is in pneumatic connection with the rear side of the nonreturn valve 12 via the equalization line 100 and thus with the second gas port 3. An equalization volume flow 110 thus flows from the equalization space 9 in the direction of the second gas port 3 as soon as the pressure level in the equalization space 9 is higher than the pressure level in the second gas port 3. The pneumatic connection with the second gas port 3 by means of the equalization line 100 of the dispensing element 10 makes it possible for the volume of the equalization space 9 to be able to be selected to be smaller than in the solutions according to FIGS. 1, 2a, 2b, 3a, 3b, in which the dispensing element 10 is in pneumatic connection with the environment 33 (FIG. 1).

Figure 5:
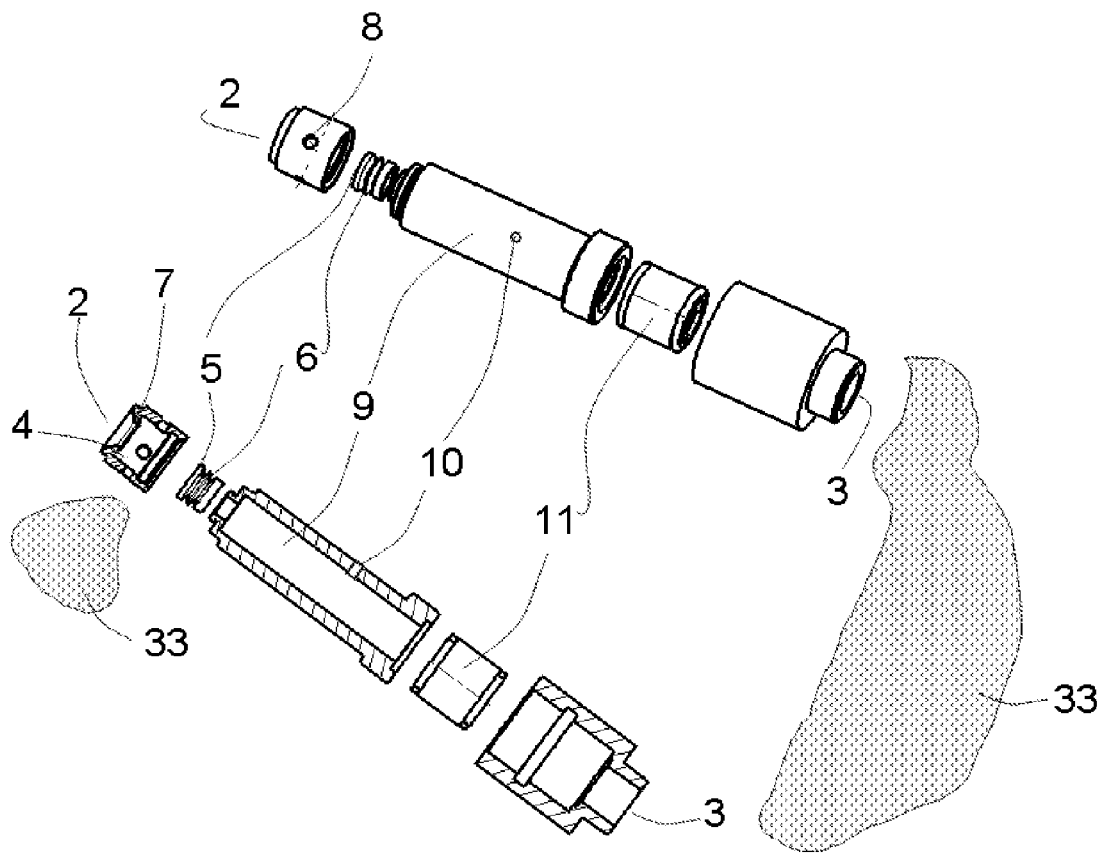
FIG. 5 is a perspective exploded view and aa cross sectional exploded view showing another view of the pressure relief unit according to FIG. 1.

FIG. 5 shows a pressure relief unit 1 according to the present invention according to FIG. 1 in a combination of a three-dimensional view and a longitudinal section.

Identical elements in FIG. 5 are designated by the same reference numbers as in FIG. 1.

The pressure relief unit 1 comprises a first gas port 2, a second gas port 3 to an environment 33, a relief valve 4, a pressure relief outlet 8, an equalization space 9, a dispensing element 10, and a nonreturn valve 11. The relief valve 4 comprises a valve disk 5 with a valve seat 7. The valve disk 5 is connected with a space 9 via a flexible bellows 6 in a gas-tight manner. An equalization space 9 is used as a pressure storage means and is closed on the side of the second gas outlet 3 by the nonreturn valve 11. Equalization space 9 has an opening into the environment 33 via a dispensing element 10. The valve disk 5 is pressed by a horizontal motion against the sealing crater 7 in case of a correspondingly great difference between the operating pressure $p_w$ and the pressure $p_V$ in space 9 and thus closes the pressure relief outlet 8 between the first gas port and the environment 33.

While specific embodiments of the invention have been described in detail to illustrate the application of the principles of the invention, it will be understood that the invention may be embodied otherwise without departing from such principles.

| List of Reference Numbers | |
| --- | --- |
| 1 | Pressure relief unit |
| 2 | First gas port |
| 3 | Second gas port |
| 4 | Relief valve |
| 5 | Valve disk |
| 6 | Bellows |
| 7 | Valve seat |
| 8 | Pressure relief outlet |
| 9 | Equalization space |
| 10 | Dispensing element |
| 11 | Nonreturn valve |
| 12 | Nonreturn valve sealing element |
| 13 | Nonreturn valve seat |
| 20 | Main stream branch |
| 21, 23 | Operating pressure levels $p_{w,1}$, $p_{w,2}$ |
| 22, 24 | Pressure level in the equalization space $p_{V,1}$, $p_{V,2}$ |
| 25, 27 | Front-side pressures $p_{F,1}$ |
| 26, 28 | Rear-side pressure $p_{B,1}$, $p_{B,2}$ |
| 30 | Bypass stream branch |
| 33 | Environment |
| 40 | Volume flow |
| 41 | Volume flow component |
| 43, 45 | Front-side forces $F_{F,1}$, $F_{F,2}$ |
| 44, 46 | Rear-side forces $F_{B,1}$, $F_{B,2}$ |
| 50 | Electromechanically driven medical gas delivery means |
| 51 | Front-side surface A1 |
| 52 | Rear-side surface A2 |
| 60 | Respirator, medical device for respirating a patient |
| 66 | Closing means |
| 67 | Feed lines |
| 70 | Patient |
| 100 | Equalization line |
| 110 | Equalization volume flow |

What is claimed is:

1. A pressure relief device for pressure equalization for an electromechanically driven medical gas delivery means in a medical device for respirating a patient with a gas volume flow which is adapted to an operating state of the medical device for respirating the patient and to an operating state of the electromechanically driven medical gas delivery means, the pressure relief device comprising:
    a first gas port;
    a second gas port;
    a relief valve with a valve disk and a valve seat;
    a bypass stream branch connecting the first gas port to the relief valve;
    a pressure relief outlet;
    an equalization space; and
    a nonreturn valve, the equalization space connecting the second gas port to the relief valve via the nonreturn valve, the valve disk being in pneumatic connection with the electromechanically driven medical gas delivery means via a front-side surface area and via a rear-side surface area, wherein:
    the front-side surface area is made larger than the rear-side surface area and a front-side force acts on the valve disk via the front-side surface area and a rear-side force acts on the valve disk via the rear-side surface area at an operating pressure and a pressure level in the equalization space;
    a distance between the valve disk and the valve seat is determined by an operating pressure and a prevailing pressure in the equalization space and by a ratio of the front-side surface area to the rear-side surface area and by a ratio of the front-side force to the rear-side force, so that a partial volume flow, of the gas volume flow, flows off into the environment via the bypass stream branch, via the relief valve and via the pressure relief outlet.

2. A device in accordance with claim 1, further comprising a main stream branch through which the gas volume flow passes, each of the first gas port and the second gas port being connected to the main stream branch wherein:
    the relief valve opens and the valve disk partially releases the pressure relief outlet in a case with the front-side force greater than the rear-side force, whereby the partial volume flow of the gas volume flow in the main stream branch or the total gas volume flow flows off into the environment via the bypass stream branch and via the pressure relief outlet.

3. A device in accordance with claim 1, wherein the relief valve closes and the valve disk completely or partially closes the pressure relief outlet in a case in which the front-side force is weaker than the rear-side force, so that a small partial volume flow or no partial volume flow or no gas volume flow flows off into the environment from the main stream branch via the pressure relief outlet and via the bypass stream branch.

4. A device in accordance with claim 1, wherein the relief valve further comprises an elastic or partially elastic bellows and the valve disk is held with the elastic or partially elastic bellows in the relief valve.

5. A device in accordance with claim 4, wherein the bellows is made elastic or partially elastic in such a way that the valve disk is arranged by a prestress in a preferred position in the direction of the valve seat.

6. A device in accordance with claim 4, wherein the bellows is made elastic or partially elastic in such a way that the valve disk is arranged in the direction of the valve seat without a prestress and without a preferred position.

7. A device in accordance with claim 1, further comprising:
    a main stream branch through which the gas volume flow passes, each of the first gas port and the second gas port being connected to the main stream branch; and
    a dispensing element in pneumatic connection with the equalization space and in a pneumatic connection with one of the environment and an equalization line connected with the main stream branch carrying the air flow from the gas delivery means to the medical device for respirating the patient, the dispensing element for equalizing pressure in the equalization space with the pressure in the environment or with the pressure in the main stream branch.

8. A device in accordance with claim 7, wherein the dispensing element defines time interval of 3 to 6 minutes for pressure equalization between the equalization space and the environment or between the equalization space and the main stream branch carrying the air flow from the gas delivery means to the medical device for respirating a patient.

9. A device in accordance with claim 1, wherein the electromechanically driven gas delivery means comprises a radial flow compressor.

10. A device in accordance with claim 1, wherein the electromechanically driven gas delivery means comprises a rotary compressor.

11. A medical system comprising:
an electromechanically driven medical gas delivery device;
a medical device for respirating a patient with a gas volume flow;
a main gas stream branch through which the gas volume flow passes from the gas delivery device to the medical device for respirating the patient; and
a pressure relief device comprising:
a first gas port;
a second gas port, each of said first gas port and said second gas port being connected to said main gas stream branch;
a pressure relief outlet;
a relief valve with a valve disk and a valve seat, said valve disk blocking gas flow from said first gas port to said pressure relief outlet with said valve disk seated on said valve seat and allowing gas flow from said first gas port to said pressure relief outlet depending on a distance between the valve disk and the valve seat;
an equalization space; and
a nonreturn valve, said equalization space connecting said second gas port to said relief valve via said nonreturn valve, said valve disk having a first side surface area exposed to gas pressure prevailing in said main gas stream branch and having a second side surface area exposed to gas pressure prevailing in said equalization space, said first side surface area being larger than said second side surface area with an operating gas pressure of said main gas stream branch resulting in a first side force acting on the valve disk via said first side surface area and a gas pressure of said equalization space resulting in a second side force acting on the valve disk via said second side surface area to determine the distance between the valve disk and the valve seat to regulate a partial volume flow, of the gas volume flow, flowing to the pressure relief outlet.

12. A device in accordance with claim 11, wherein the relief valve closes or partially closes the pressure relief outlet in a case in which the first side force is weaker than the second side force, so that a small partial volume flow or no partial volume flows to the pressure relief outlet.

13. A system in accordance with claim 11, wherein the relief valve further comprises an elastic or partially elastic bellows and the valve disk is held with the elastic or partially elastic bellows in the relief valve.

14. A system in accordance with claim 13, wherein the bellows is made elastic or partially elastic in such a way that the valve disk is arranged by a prestress in a preferred position in the direction of the valve seat.

15. A system in accordance with claim 13, wherein the bellows is made elastic or partially elastic in such a way that the valve disk is arranged in the direction of the valve seat without a prestress and without a preferred position.

16. A system in accordance with claim 11, further comprising:
a dispensing element in pneumatic connection with the equalization space and in pneumatic connection with one of the environment and with an equalization line formed by the second port and connected with the main gas stream branch carrying the air flow from the gas delivery device to the medical device for respirating the patient, the dispensing element for equalizing pressure in the equalization space with the pressure in the environment or with the pressure in the main gas stream branch.

17. A system in accordance with claim 16, wherein the dispensing element defines a time interval of 3 to 6 minutes for pressure equalization between the equalization space and the environment or between the equalization space and the main stream branch carrying the air flow from the gas delivery device to the medical device for respirating a patient.

18. A system in accordance with claim 11, wherein the electromechanically driven gas delivery device comprises a radial flow compressor.

19. A system in accordance with claim 11, wherein the electromechanically driven gas delivery device comprises a rotary compressor.

20. A pressure relief device for pressure equalization for a main gas stream branch through which a gas volume flow passes from a gas delivery means to a medical device for respirating a patient, the pressure relief device comprising:
a first gas port;
a second gas port, each of said first gas port and said second gas port being connected to said main gas stream branch;
a pressure relief outlet;
a relief valve with a valve disk and a valve seat, said valve disk blocking gas flow from said first gas port to said pressure relief outlet with said valve disk seated on said valve seat and allowing gas flow from said first gas port to said pressure relief outlet depending on a distance between the valve disk and the valve seat;
an equalization space; and
a nonreturn valve, said equalization space connecting said second gas port to said relief valve via said nonreturn valve, said valve disk having a first side surface area exposed to gas pressure prevailing in said main gas stream branch and having a second side surface area exposed to gas pressure prevailing in said equalization space, said first side surface area being larger than said second side surface area with an operating gas pressure of said main gas stream branch resulting in a first side force acting on the valve disk via said first side surface area and a gas pressure of said equalization space resulting in a second side force acting on the valve disk via said second side surface area to determine the distance between the valve disk and the valve seat to regulate a partial volume flow, of the gas volume flow, flowing to the pressure relief outlet.

* * * * *